(12) United States Patent
Parthasarathy et al.

(10) Patent No.: US 10,758,700 B2
(45) Date of Patent: Sep. 1, 2020

(54) HOME-BASED HELIOX SYSTEM WITH CARBON DIOXIDE REMOVAL

(71) Applicant: The Arizona Board of Regents on behalf of the University of Arizona, Tucson, AZ (US)

(72) Inventors: Sairam Parthasarathy, Tucson, AZ (US); Marvin J. Slepian, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 666 days.

(21) Appl. No.: 15/026,039

(22) PCT Filed: Sep. 30, 2014

(86) PCT No.: PCT/US2014/058368
§ 371 (c)(1),
(2) Date: Mar. 30, 2016

(87) PCT Pub. No.: WO2015/048766
PCT Pub. Date: Apr. 2, 2015

(65) Prior Publication Data
US 2016/0213879 A1    Jul. 28, 2016

Related U.S. Application Data

(60) Provisional application No. 61/884,654, filed on Sep. 30, 2013.

(51) Int. Cl.
*A61M 16/12*     (2006.01)
*A61M 16/00*     (2006.01)
(Continued)

(52) U.S. Cl.
CPC ........ *A61M 16/12* (2013.01); *A61M 16/0069* (2014.02); *A61M 16/0078* (2013.01);
(Continued)

(58) Field of Classification Search
CPC .. A61M 2202/0007; A61M 2202/0208; A61M 2202/025; A61M 2230/005;
(Continued)

(56) References Cited

U.S. PATENT DOCUMENTS 3,385,293 A    5/1968    Phillips et al.
3,710,553 A    1/1973    Parker et al.
(Continued)

FOREIGN PATENT DOCUMENTS

| CN | 2319062 Y | 5/1999 |
| WO | WO 2011/106629 | 9/2011 |
| WO | WO2011106629 | 9/2011 |

OTHER PUBLICATIONS

Arayen Trade, "Self-Contained Breathing Apparatus", http://arayemtrade.com/sabre_self_contained_breathing_apparatus, 10 pages, retrieved from the internet Sep. 25, 2013.
(Continued)

*Primary Examiner* — Tu A Vo
*Assistant Examiner* — Alexander Morales
(74) *Attorney, Agent, or Firm* — Pabst Patent Group LLP (57) ABSTRACT

A closed-circuit heliox delivery system and methods for alleviating symptoms of COPD and related disorders are provided. The system is self-monitoring and can be used outside of a hospital environment. The system contains a gas supply fluidly connected to a breathing circuit. The breathing circuit contains an upper airway device, such as a mask. The system contains a sensor(s) and controller. The sensors measure parameters in the system, the ambient environment, or related to the physiological state of the user. The con-
(Continued)

troller can adjust the system to maintain parameters within the device, i.e. pressure, temperature, humidity, within predetermined ranges. The controller can adjust the system to maintain a target physiological state of the user, i.e. target blood oxygen levels or Work of Breathing (WOB).

30 Claims, 4 Drawing Sheets

(51) Int. Cl.
  *A61M 16/22* (2006.01)
  *A61M 16/08* (2006.01)
  *A61M 16/16* (2006.01)
  *A61M 16/20* (2006.01)
  *A61M 16/10* (2006.01)

(52) U.S. Cl.
  CPC ...... *A61M 16/0891* (2014.02); *A61M 16/161* (2014.02); *A61M 16/202* (2014.02); *A61M 16/208* (2013.01); *A61M 16/22* (2013.01); A61M 2016/0021 (2013.01); A61M 2016/0027 (2013.01); A61M 2016/0039 (2013.01); A61M 2016/103 (2013.01); A61M 2016/1025 (2013.01); A61M 2202/025 (2013.01); A61M 2202/0208 (2013.01); A61M 2205/3303 (2013.01); A61M 2230/06 (2013.01); A61M 2230/205 (2013.01)

(58) Field of Classification Search
  CPC ........ A61M 2230/06; A61M 2230/205; A61M 16/0069; A61M 16/0078; A61M 16/0891; A61M 16/12; A61M 16/161; A61M 16/202; A61M 16/208; A61M 16/22; A61M 2016/0021; A61M 2016/0027; A61M 2016/0039; A61M 2016/1025; A61M 2016/103; A61M 2205/3303
  USPC ............. 128/203.14, 204.21, 205.11, 207.18
  See application file for complete search history.

(56) References Cited

U.S. PATENT DOCUMENTS

| | | | |
|---|---|---|---|
| 4,883,051 A | | 11/1989 | Westenskow et al. |
| 5,429,123 A | | 7/1995 | Shaffer et al. |
| 6,760,610 B2 | * | 7/2004 | Tschupp ............... A61B 5/0002 600/309 |
| 6,983,749 B2 | | 1/2006 | Kumar et al. |
| 9,724,483 B2 | * | 8/2017 | Hyde ....................... G06F 19/00 128/200.24 |
| 10,058,664 B2 | * | 8/2018 | Kimm ................ A61M 16/0096 |
| 2003/0106554 A1 | | 6/2003 | de Silva et al. |
| 2004/0074251 A1 | * | 4/2004 | Shahbaz ............... F24F 13/222 62/305 |
| 2004/0129270 A1 | * | 7/2004 | Fishman ........... A61M 16/0051 128/204.18 |
| 2004/0254501 A1 | * | 12/2004 | Mault .................... A61B 5/083 600/587 |
| 2006/0174889 A1 | * | 8/2006 | Noble ............... A61M 16/0666 128/206.11 |
| 2006/0194091 A1 | * | 8/2006 | Strohl ............... H01M 8/04097 429/415 |
| 2006/0283450 A1 | * | 12/2006 | Shissler ............ A61M 16/0063 128/204.21 |
| 2007/0163591 A1 | * | 7/2007 | Ross ...................... A62B 19/00 128/205.12 |
| 2008/0066741 A1 | * | 3/2008 | LeMahieu ............ A61M 11/041 128/200.21 |
| 2008/0078385 A1 | * | 4/2008 | Xiao .................. A61M 16/1075 128/203.26 |
| 2010/0139659 A1 | | 6/2010 | von Blumenthal |
| 2010/0224191 A1 | * | 9/2010 | Dixon .................... A61B 5/145 128/204.23 |
| 2013/0040365 A1 | | 2/2013 | Vander Horn et al. |
| 2013/0340753 A1 | * | 12/2013 | Weiszl .................. A61M 16/20 128/203.14 |
| 2014/0277756 A1 | * | 9/2014 | Bruce .................... G05D 22/02 700/276 |
| 2015/0000655 A1 | * | 1/2015 | Desilva ..................... G01F 1/50 128/203.14 |

OTHER PUBLICATIONS

Chatmongkolchart, et al., "Heliox delivery with noninvasive pressure ventilation: a laboratory study", *Respir Care*, 46(3):248-54 (2001).

Clinical Trial, "Continuous or nocturnal oxygen therapy in hypoxemic chronic obstructive lung disease: a clinical trial. Nocturnal oxygen therapy trial group", *Ann Interm Med.*, 93(3):391-8 (1980).

COPD, Chronic Obstructive pulmonary disease (COPD), Fact sheet, National Inst of Health, last updated Oct. 2010.

Drager, "Drager PSS® BG 4 closed-circuit breathing apparatus", http://www.draeger.com/sites/enus_us/Pages/Fire-Services/Draeger-PSS-BG-4-plus.aspx, 5 pages downloaded from the internet Sep. 25, 2013.

Fogel, et al., "Genioglossal activation in patients with obstructive sleep apnea versus control subjects", *Am J Crit Care Med.*, 164:20325-30 (2001).

Kass and Castriotta, "Heliox therapy in acute severe asthma", *Chest*, 107(3):757-60 (1995).

Malhotra, et al., "Pharyngeal pressure and flow effects on genioglossus activation in normal subjects", *Am J Respir Crit Care Med.*, 165:71-7 (2002).

Martinon-Torres, et al., "Heliox therapy in infants with acute bronchiolitis", *Pediactrics*, 109(1):68-73(2002).

O'Callaghan, et al., "The Effects of Heliox on the Output and Particle-Size Distribution of Salbutamol Using Jet and Vibrating Mesh Nebulizers", *J Aerosol Med.*, 20(4): 434-44 (2007).

Palange, et al., "Effect of heliox on lung dynamic hyperinflation, dyspnea, and exercise endurance capacity in COPD patients", *J Appl Physiol*, 97:1637-42 (2003).

Reuben and Harris, "Heliox for asthma in the emergency department: a review of the literature", *Emerg Med J*, 21: 131-5 (2004).

Wedzicha, "Heliox in chronic obstructive pulmonary disease: lightening the airflow", *Am J Respiratory and Critical Care Medicine*, 173(8):825-6 (2006).

Clinical Trial, "Continuous or nocturnal oxygen therapy in hypoxemic chronic obstructive lung disease: a clinical trial. Nocturnal oxygen therapy trial group", Ann Interm Med., 93(3):391-8 (1980).

COPD, Chronic Obstrutive pulmonary disease (COPD), Fact sheet, National Inst of Health, last updated Oct. 2010.

International Search Report for corresponding PCT application PCT/US2014/058368 dated Jan. 15, 2015.

* cited by examiner

HOME-BASED HELIOX SYSTEM WITH CARBON DIOXIDE REMOVAL

CROSS-REFERENCE TO RELATED APPLICATION

The present application is a 371 application of International Application No. PCT/US2014/058368, which claims benefit and priority U.S. Provisional Application No. 61/884,654, filed Sep. 30, 2013, all of which are incorporated herein by reference.

FIELD OF THE INVENTION

This invention relates generally to systems and methods for alleviating the symptoms of COPD and related diseases and disorders.

BACKGROUND OF THE INVENTION

Chronic obstructive pulmonary disease (COPD) is a chronic, slowly progressive disorder characterized by airflow obstruction (associated with aberrant airway inflammation) and airway remodeling. COPD symptoms can present with airway tissue damage. Airflow limitation is slowly progressive, leading to dyspnoea and limitations of physical exercise capacities. However, impairment is not restricted to the lungs, as COPD patients are also at higher risk for systemic failures including cardiovascular diseases.

The clinical presentation of COPD can vary in severity from simple chronic bronchitis without disability to a severely disabled state with chronic respiratory failure. The diagnosis of COPD is usually suggested by symptoms, but is typically only established by quantitative measurements, preferably using spirometry.

COPD is the fourth leading causes of death worldwide and the only major disease with an increasing death rate. By 2020, it is estimated that only ischemic heart disease and cerebrovascular disease will account for a higher mortality among the world's population. Prevalence and hospitalization rates have increased dramatically over the past years. According to statistics from the National Institute of Health (NIH), 12 million adults in the U.S. are diagnosed with COPD, and 120,000 die from it each year. An additional 12 million adults in the U.S. are thought to have undiagnosed COPD. COPD accounts for 1.5 million emergency room visits and over 700,000 hospitalizations annually, with an estimated cost to the US healthcare system of over $32.1 billion in 2001. COPD death rates for women have risen steadily. Today, more women than men die from COPD each year.

There is a scarcity of available information and extremely low public awareness about COPD. There are few efficacious alternative treatments available. Lack of awareness and the insidious nature of the disease have been major contributing factors to the low diagnostic rates seen in COPD. As the symptoms of the disease occur with the onset of middle age, many patients dismiss symptoms such as breathlessness upon exertion as old age. Smokers, who constitute the majority of COPD sufferers, also commonly dismiss symptoms, such as chronic cough, as something to be expected because of smoking, rather than an indication of a serious underlying problem.

The Nocturnal Oxygen Therapy Trial supported by the NIH showed that patients with advanced COPD live longer with long-term oxygen therapy. Clinical trials sponsored by the National Heart, Lung, and Blood Institute and the Centers for Medicare and Medicaid Services are investigating the effectiveness of oxygen treatment for increasing life expectancy in patients with moderate COPD.

Heliox is a breathing gas composed of a mixture of Helium (He) and Oxygen ($O_2$). Heliox generates less airway resistance than air and requires less mechanical energy to ventilate the lungs, reducing the Work of Breathing (WOB). While oxygen alone may reduce breathlessness, heliox reduces resistance in the lungs during exhalation, which allows COPD patients to exhale more air. This means the lungs can better eliminate carbon dioxide from the body. According to results of a randomized, crossover trial, a combination of helium and oxygen improves walking distance in patients with COPD. Wedzicha, *American Journal of Respiratory and Critical Care Medicine,* 173(8):825-826 (2006). In another, smaller study, giving heliox during exercise allowed a greater amount of air to be inhaled by the lungs and reduced shortness of breath scores compared to those who were on room air. Heliox induced a state of hyperventilation, which reduced carbon dioxide levels in the blood of patients studied, increasing exercise capacity. See Palange et al., *J Appl Physiol,* 97:1637-1642 (2003).

Although medical uses of heliox have been known since the 1930s, it is typically only administered in settings such as a hospital or modern specialist respiratory centers. Systems used in these settings rely on an invasive ventilator system or non-invasive open-circuit breathing systems to deliver heliox treatment. Open-circuit breathing systems are inefficient for delivery of heliox because a portion of the gas escapes into the atmosphere prior to reaching a patient's lungs and helium is lost to the atmosphere upon exhalation. This results in as many as four to six full-sized tanks of heliox being required for 24 hours of treatment. Helium is over 13 times as expensive as oxygen. Therefore, current heliox treatments are inconvenient and cost-prohibitive for many patients.

Closed-circuit breathing apparatuses have been developed for applications requiring complete respiratory protection in potentially hazardous conditions, such as decontamination, urban search and rescue, or biohazard situations. Exhaled carbon dioxide is typically removed by an in-line carbon dioxide scrubbing device. These systems typically deliver only pure oxygen or standard or enhanced breathing air mixture, similar to that used during scuba diving. Currently available closed-circuit breathing apparatuses are not configured to regulate a mixture of heliox. Further, current closed-circuit breathing apparatuses can only function for limited durations (e.g. 4 hours or less). Thus, current closed-circuit breathing apparatuses are not suitable for long term (i.e. overnight) use.

The amount of oxygen within the closed-circuit is regulated by standard in-line and/or tank regulator that is manually adjusted prior to or during use. Therefore, a user must be conscious in order to operate the breathing apparatus. As such, current closed-circuit breathing apparatus are unsuitable for use in sleeping or otherwise unconscious individuals.

There exists a need for improved heliox treatments.

It is therefore an object of the invention to provide improved systems and methods for heliox delivery to an individual suffering from COPD or symptoms thereof or related diseases or disorders.

It is a further object of the invention to provide more cost effective systems and methods for heliox delivery.

It is an additional object of the invention to provide systems and methods for heliox delivery that can be routinely employed outside the hospital setting, such as in a patient's home.

SUMMARY OF THE INVENTION

A closed-circuit heliox delivery system is provided. The system is useful for alleviating one or more symptoms of COPD and related disorders. COPD disorders and symptoms include, but are not limited to, emphysema, chronic bronchitis, chronic airflow limitation, chronic airways obstruction, non-reversible obstructive airways disease, chronic obstructive airways disease and chronic obstructive lung disease.

The closed-circuit heliox delivery system is simple for individual operation and sufficiently compact to be used in an at-home setting, and is optionally portable. The closed-circuit heliox delivery system provides a more convenient and less expensive alternative to conventional heliox delivery systems for patients with COPD or related diseases and disorders.

The closed-circuit heliox delivery system contains a breathing circuit configured to receive helium, oxygen, and mixtures thereof or mixtures with other suitable gases from a gas supply. The closed-circuit heliox delivery system contains an upper airway device, typically a mask, configured to deliver an inhaled volume of gas to an, individual or patient in need thereof and to receive an expired volume of gas. The closed-circuit heliox delivery system contains a carbon dioxide removal system for removing $CO_2$ from the expired gas mixture. The closed-circuit heliox delivery system also contains one or more sensors operably connected to a controller. The sensors can monitor one or more parameters related to conditions within the device, one or more parameters related to the ambient conditions, one or more parameters related to the physiological state of the user, or a combination thereof. For example, the sensors may monitor the partial pressure of the gases in the breathing circuit. The closed-circuit heliox delivery system can contain additional sensors, for instance for monitoring the temperature, humidity, etc.

The system contains a controller. The controller receives one or more parameters from the sensor(s) and can adjust one or more components of the device in response to the parameter(s) to maintain target conditions within the device, to maintain a target physiological state of the user, or a combination thereof. For example, the controller can adjust the flow of supply gases, such as helium, oxygen, or a combination thereof, to maintain the ratio of gases in the breathing circuit within a preset target range.

Optionally, one or more pharmaceutical or diagnostic agents are administered in the system.

A method of using a closed-circuit heliox delivery system to administer heliox to a patient or individual in need thereof is also provided. The patient or individual in need of heliox administration breathes normally through an upper airway device. The upper airway device is suitable for use with a closed-circuit heliox delivery system, and is preferably a mask or other suitable device that covers the mouth and nasal openings.

The closed-circuit heliox delivery system is self-monitoring, allowing the patient or individual in need of heliox delivery to sleep or to perform other tasks during heliox administration.

DETAILED DESCRIPTION OF THE INVENTION

I. Closed-Circuit Heliox Delivery System

A. Breathing Circuit

"Breathing circuit" as used herein generally refers to the system of hoses or tubing that connect the patient to the closed-circuit heliox delivery system. The breathing circuit carries gases from the gas supply to the patient and returns the expired gases to the carbon dioxide removal systems. The breathing circuit contains an inspiratory portion for delivering heliox to the patient and an expiratory portion that delivers expired gases from the patient to a Heliox recycler and Carbon Dioxide removal system.

For example, a typical breathing circuit may contain: (1) an inspiratory conduit that delivers a fresh Heliox mixture to the patient; (2) an expiratory conduit that delivers expired gases from the patient to a Heliox recycler and Carbon Dioxide removal system; (3) a mask or other suitable upper airway device to deliver gases in and out of the lungs; and (4) a connector to connect the inspiratory and expiratory conduits to the upper airway device, such as a Y- or T-connector. Other components may be added as required, such as a nebulizing device to aerosolize and deliver additional therapeutic and/or diagnostic agents, and humidifiers and/or dehumidifiers to control air moisture. Optionally, a humidifier may be used to deliver additional therapeutic and/or diagnostic agents, particularly those in particulate form that can be aerosolized.

Often, the inspiratory and expiratory conduits are made of disposable corrugated plastic or rubber hoses or tubing. Hoses generally have larger diameters than tubing. Hoses may have a corrugated design to allow bending of the hose while preventing twisting of the hose or cutting off of flow through the hose. Standard corrugated medical hoses may be used in the system and come with internal diameters of 6 mm, 10 mm, 15, mm, 19 mm, 22 mm, 25 mm, and 32 mm and in ranging from 6 inches to more than 10 feet.

The breathing circuit may contain a counterlung, such as a chamber or breathing bag, configured to receive an expired gas volume and for providing a gas volume to the inspiratory conduit. The chamber or breathing bag is configured to allow the patient to take in a deep breath without dropping the pressure in the closed circuit to less than 0 cm $H_2O$. The breathing circuit may contain one or more safety valves and/or connection ports, for example for operably connecting sensors, pulmonary delivery devices, and/or humidity control devices to the breathing circuit.

The breathing circuit typically contains one or more valves. For example, one or more one-way valves may be provided to direct gas flow in only one direction through the breathing circuit. Other valves may be included to open the breathing circuit to the outside environment.

Preferably, the closed-circuit heliox delivery system contains a valve that opens upon receiving a stimulus, wherein the opening of the valve exposes the breathing circuit to the external atmosphere. In this way, the valve can act as a safety mechanism to prevent suffocation. The stimulus to trigger a valve to open or close can be an amount of a gas within the breathing circuit or any type of signal (e.g. electrical, wireless, optical, or otherwise) transmitted from the controller. This valve can be located on an upper-airway delivery device or any other location within the breathing circuit. The valve can be configured to be opened manually (e.g. by the user or attending medical practitioner) or automatically (e.g. by receiving a signal from a controller).

Figure 1:
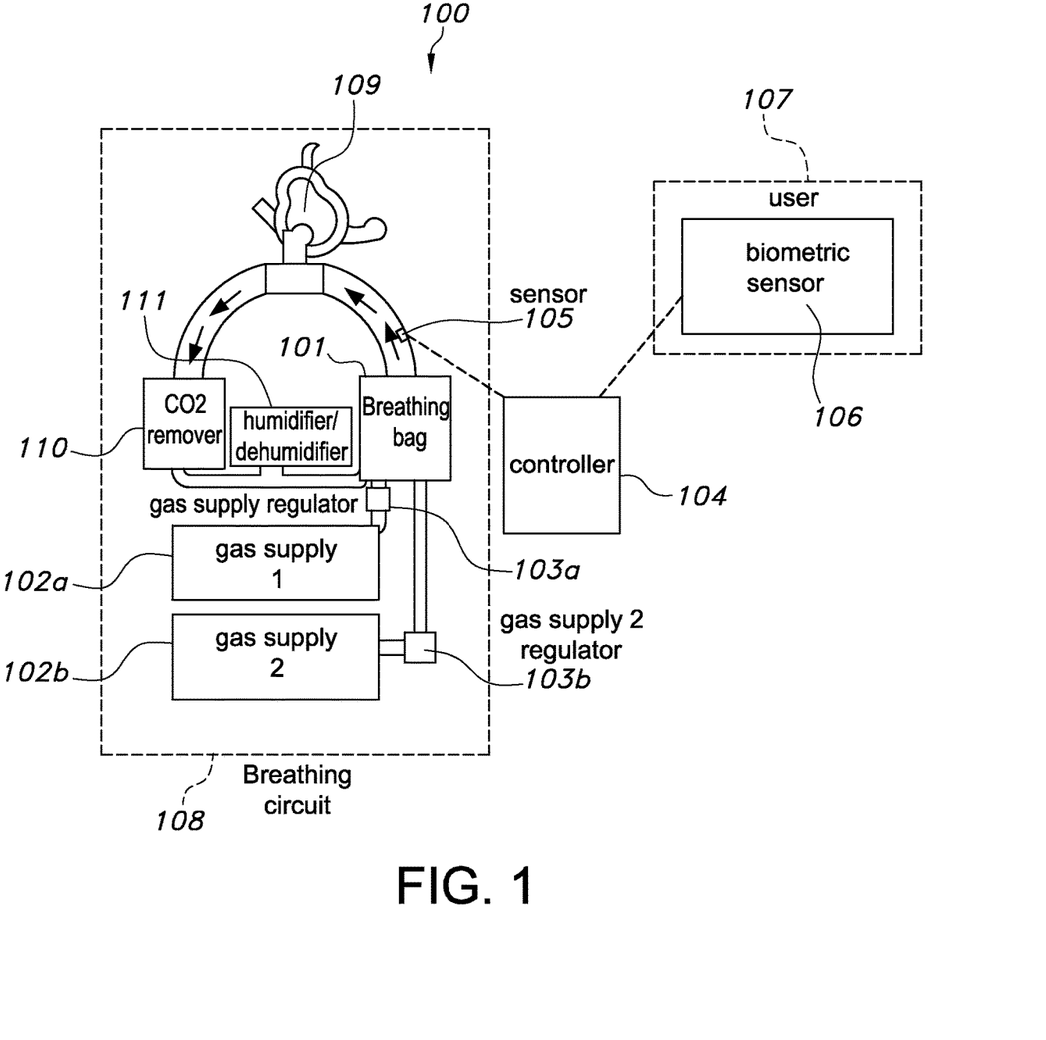
FIG. 1 is a diagram of an exemplary closed-circuit heliox delivery system. Two gas supplies are flowably connected to a breathing bag in the breathing circuit. The flow from each of the gas supplies into the breathing bag is individually controlled by the controller using a regulator. In use, the heliox mixture is drawn from the breathing bag through the inspiratory conduit, through the mask, and into the lungs of the user. The expired gases pass through the expirator conduit, into the carbon dioxide removal unit, through the humidifier/dehumidifier, and into the breathing bag. In the breathing bag the expired gases are combined with the gases flowing from the gas supplies.

Optionally, a valve is included in a port in the inspiratory portion of the circuit, such as in the breathing bag 101. The valve may be a pop-off safety valve that automatically opens when high pressure (set at greater than 5 cm $H_2O$, greater than 10 cm $H_2O$, greater than 15 cm $H_2O$, greater than 20 cm $H_2O$, or greater than 30 cm $H_2O$) is achieved within the closed circuit. The safety valve operates even if there is electrical outage and/or system failure to prevent respiratory discomfort or hazard from excessive pressure in the breathing circuitry.

The breathing circuit may contain a gas cooling device (also referred to herein as "gas cooler"). Exhaled air is warm and temperature can affect air qualities, such as relative humidity. Additionally, the removal of carbon dioxide by removal device may involve exothermic reactions which generate heat, which further increases the temperature of air within the breathing circuit. Heated gases within the breathing circuit can lead to dehydration of the sensitive lining of the patient's respiratory system (i.e. the mucous membranes) and lead to bronchospasms, respiratory distress, or even burns of the respiratory system lining. Preferably the system includes a gas cooling device that reduces the temperature of the air within the circuit prior to inhalation. In some embodiments, the breathing circuit contains a gas cooling device, which cools the air and gas mixture prior to inhalation. Preferably, the gas cooling device is incorporated into the breathing circuit downstream of the carbon dioxide removal system to regulate the temperature of the gas mixture, thereby ensuring user safety and comfort. Optionally, the cooling device is incorporated into the inspiratory conduit, prior to inhalation of the gases by the patient.

The breathing circuit may contain a humidifier, dehumidifier, or a combination humidifier/dehumidifier.

The elements of the breathing circuit, i.e. the hoses, tubes, masks, etc. may be made from any material having the requisite chemical and mechanical properties. Common materials include biocompatible organic polymers such as ethyl vinyl acetate (EVA), high-density or low-density polyethylene (PE), and polypropylene (PP), polytetrafluoroethylene (PTFE), poly(tetrafluoroethylene-co-hexafluoropropylene) (FEP), modified ethylene-tetrafluoroethylene copolymer (ETFE), polyvinylidene fluoride (PVDF), polyethylene terephthalate polyester (PET-P), derivatives thereof, copolymers thereof, and blends thereof.

i. Gas Supply

The closed-circuit heliox delivery system contains one or more gas supplies. The gas supplies are configured to deliver gas into the breathing circuit. The gas supplies can be fluidly connected to the counterlung and/or the inspiratory conduit. Gas supplies can include any means for controllably introducing a gas into the breathing circuit. The gas supplies include, but are not limited to, compressed or pressurized gas cylinders or bottles, liquefied gas sources, controlled intake of ambient air, and specialized bladders or bags. The gas supply can also include piped medical gas distribution systems found in hospitals and other medical facilities. The gas cylinders and bottles generally have a stop valve for operably c supply to the breathing circuit, typically through a pressure regulator. The pressure regulator allows high-pressure sources to be reduced to pressures usable for the closed-circuit heliox delivery system.

The gas supply is preferably a medical gas cylinder or bottle. Medical gas cylinders are available from a variety of suppliers. Medical gas cylinders are designed to meet U.S. Pharmacopeia (USP) and National Formulary (NF) standards and are manufactured in compliance with FDA current Good Manufacturing Practices (GMPs). Medical gas cylinders are typically made from high-quality steel, chromium-molybdenum allow, or aluminum, although any suitably strong and inert material may be used.

The gases provide by a gas supply generally include heliox, oxygen, or a combination thereof, although other gases may be employed. Gases provided by a gas supply include, but are not limited to, nitrogen, argon, or other inert or noble gases. Gas supplies can include mixtures of any of the above gases. Gas supplies can include ambient air or medical grade air. Medical grade air is made of approximately 78% Nitrogen and 21% oxygen with traces of water vapor, carbon dioxide, hydrogen, argon, and other components. Gas supplies can include Nitrox, a mixture of nitrogen and oxygen; Heliox, a mixture of Helium and Oxygen; or Trimix, a mixture of Helium, Nitrogen, and Oxygen.

The gas supply can include a heliox supply. Heliox refers to a mixture of gases predominantly only containing helium and oxygen gas and containing only low or trace levels of other gases or impurities. Commercially available standard heliox mixtures include from about 20% to about 30% oxygen and the remainder, i.e. from about 70% to about 80%, being helium. The heliox supply can contain 10%-50%, 10%-40%, 20%-40%, or 20%-30% oxygen, preferably the heliox supply contains about 21% oxygen. The heliox supply can contain 30%-90% helium, 50%-90% helium, or 70%-80% helium, preferably the heliox supply contains about 79% helium. The heliox supplies can come in standard pressurized gas cylinders containing, for instance, 25 $ft^3$, 42 $ft^3$, or 255 $ft^3$ of heliox.

ii. Upper Airway Device

The breathing circuit includes an upper airway device for delivering the heliox breathing mixture to a patient and receiving the expired gases from upper airway device can be a mask or an endotracheal tube, or other suitable device to deliver air to the upper airway. Preferably, the upper airway device is a mask. Most preferably, the mask provides a complete seal around the user's mouth and nose. For example, the upper airway device can be a bubble-mask that envelopes the entire head. Suitable masks are well known in the art.

The upper airway device can contain a valve or vent that can open automatically in the event of system failure, such as during an electrical outage, which allows the user to breath external environment air so as to prevent suffocation.

In other embodiments, a tent may be used to deliver heliox to a patient. In these embodiments, the user can be placed within the tent, which forms a closed breathing environment, and the atmosphere within the tent is regulated in the same way as would be if using a mask-type upper airway device.

iii. Carbon Dioxide Removal System

The closed-circuit heliox delivery system includes a carbon dioxide ($CO_2$) removal system for removal of $CO_2$ from the patient's expired gases. The carbon dioxide removal system is fluidly connected to the expiratory conduit and configured to receive the expired air. In some embodiments, the carbon dioxide removal system is fluidly connected to the counterlung and configured to deliver the expired gases into the counterlung upon $CO_2$ removal. The carbon dioxide removal system can be fluidly connected to the inspiratory conduit and configured to deliver the expired gases into the inspiratory conduit upon $CO_2$ removal.

The term "$CO_2$ removal", as used herein, refers to the removal of all or part of the $CO_2$ from the expired gas mixture. $CO_2$ removal can mean removal of greater than 80%, greater than 90%, greater than 95%, greater than 99%, or greater than 99% removal of $CO_2$ from the expired gas mixture. $CO_2$ removal can mean the resulting gas mixture contains less than 4%, less than 2%, less than 1%, less than 0.1%, or about 0.04% $CO_2$.

The carbon dioxide removal system can be a chamber, reactor bed, vessel, etc. containing a carbon dioxide sorbent material. The carbon dioxide removal system can contain a non-reversible chemical fixation sorbent, such as sodium hydroxide, calcium hydroxide, lithium hydroxide, or potassium hydroxide that reacts with the $CO_2$ to produce the corresponding carbonate and water. The non-re fixation sorbent can be a peroxide capable of absorbing large amounts of $CO_2$ per unit weight, such as sodium peroxide or lithium peroxide. The peroxides have the added benefit of producing oxygen gas from the reaction with $CO_2$.

The carbon dioxide removal system can include a reversible chemical fixation sorbent, such as liquid amines. Liquid amines, such as monoethanolamine, are capable of binding $CO_2$ at low temperatures and releasing $CO_2$ upon heating.

The carbon dioxide removal system can contain a membrane that acts as a filter to separate the carbon dioxide from the other gases. Polymeric membranes can act as a molecular sieve or can separate the gases based on solution diffusion. Membranes can contain pores of a controlled size relative to the kinetic (sieving) diameter of the gas molecule. The membranes can be made of organic or inorganic compounds.

The membrane can be polymeric. The polymeric membrane can be porous and act as a molecular sieve, or non-porous and separate gases based on their solubility within the polymeric membrane as well as their physical-chemical interaction with the polymer. The polymeric membranes can be made out of suitable materials including, but not limited to, cellulose acetate and derivatives thereof polysulfones, polyimidies, polyvinyl acetate, and combinations of polymers, such as blends of polyimides. The polymeric membrane can be a mixed matrix membrane in which an organic polymer is combined with an inorganic compound to generate the membrane.

The carbon dioxide removal system optionally includes a molecular sieve. The molecular sieve can contain silicate, silicone rubber, or zeolites, which are crystalline materials composed of silicon and aluminum (aluminosilicate).

The carbon dioxide removal system can contain activated carbon, which absorbs carbon dioxide from the expired air.

vi. Regulators

The closed-circuit heliox delivery system contains one or more regulators or other means for automatically controlling the flow of one or more of the gas supplies into the breathing circuit.

Each gas supply can be equipped with a regulator that can be used to control the flow of gas from the gas supply. Additional regulators can be p along the breathing circuit to allow for additional control of the breathing circuit. The regulators can be configured to be manually controlled or electronically controlled by a controller.

vii. Delivery of Therapeutic Agents

Optionally, one or more therapeutic or diagnostic agents are administered to a patient via the heliox delivery system. The agent can be any suitable agent that can be aerosolized. Exemplary therapeutic agents include but are not limited to bronchodilators, such as beta mimetics, anticholinergics, anti-inflammatory agents, steroids, and mast cell stabilizers. Exemplary biological agents include but are not limited to proteins, peptides, cells, and other biological agents.

The agents can be administered continuously or intermittently, in any desired pattern.

The agents can be administered via a humidifier. For example, an ultrasonic humidifier can be used in the system to ensure proper humidity levels for the gas mixture and optionally, can be used to aerosolize one or more therapeutic agents. Preferably the agents are effective at facilitating lung mechanics to improve breathing. For example, a bronchodilator may be administered to a patient with shallow breathing.

The system described herein can be used to administer one or more therapeutic agents to a patient while the patient sleeps. During a normal sleep period, humans experience a change in bronchial tone over time, which follows a standard circadian rhythm. Typically, the worst bronchial tone is present in the middle of the night, such as around 2-5 am, typically around 4 am. The amount of time since the last dose of a bronchodilator also impacts bronchial tone, with decreases in bronchial tone over time, such as over a period of 4 to 6 hours since the previous dose.

The system described herein can include one or more biometric sensors, such as biometric sensors that measure transcutaneous $CO_2$, to provide data to the controller to determine the quality of the patient's breathing. If data indicate shallow breathing (such as determined by measurements from a spirometer) and/or acoustic vibrations that are consistent with wheezing in the breathing circuit, then the system releases an effective amount of the one or more therapeutic agents in the inspiratory conduit, prior to inhalation of the gases by the patient, to improve allows a patient to sleep through the night, while receiving the necessary medication to improve breathing.

The presence of helium in the system can facilitate delivery of the one or more therapeutic agents to the deep lung. Additionally, small particles (e.g. less than 5 microns in diameter) containing the one or more therapeutic agents may be stabilized by helium. See, O'Callaghan, et al., "*The Effects of Heliox on the Output and Particle-Size Distribution of Salbutamol Using Jet and Vibrating Mesh Nebulizers*", Journal of Aerosol Medicine, 20(4): 434-444 (December 2007).

B. Sensors

The closed-circuit heliox delivery system can contain sensors for measuring various parameters in the device, for measuring various parameters in the ambient environment outside the device, and/or for measuring various parameters within the patient. A variety of microsensors and microelectromechanical sensors (MEMS)-based sensors are commercially available, including MEMS biosensors for detecting specific chemical or biological pathogens, MEMS pressure or temperature sensors, etc i. Sensors for Detecting Conditions Within the Breathing Circuit The closed-circuit heliox delivery system can contain sensors for measuring parameters within the device. The sensors can be positioned within the device or, in some cases, can be positioned exterior to the device. For example, a sensor for measuring the volumetric flow rate within the device might be placed within the inspiratory conduit, within the expiratory conduit, or both. A sensor for measuring the presence of an analyte within the expired gas mixture might, however, be an optical sensor positioned on the exterior of the expiratory conduit.

The system may include one or more acoustic sensors. The acoustic measures may be configured to measure acoustic signals associated with different breathing conditions such as shallow breathing, wheezing, and/or normal breathing.

Parameters to be measured within the breathing circuit can include linear flow rate, volumetric flow rate, flow patterns within and across breaths, total pressure, fluctuations in pressure within and outside the respiratory frequency range, hours of operation, hours of operation over a specified (e.g. 12-month) time period, time periods of operation of use over a specified time period (e.g. nightl operation over a 12-month time period), leak levels, change in pressure, change in flow of the chemical composition within the breathing circuit, breathing pattern and derivatives thereof, partial pressure, temperature, absolute humidity level, relative humidity level, and concentration. Pressure sensors are known in the art, including sensors for measuring the partial pressure of a particular gas. A sensor for measuring partial pressure can be an electrochemical sensor, for example a sensor for measuring partial pressure of oxygen gas may be a pO2 "Clark type" electrode.

For example, the closed-circuit heliox delivery system may include sensors for detecting the presence and/or degree of a gas leak in the system. The system may further include devices for controlling the delivery of heliox to the patient to ensure that a sufficient amount of heliox and/or oxygen is continuously administered, even in the presence of a gas leak.

ii. Sensors for Detecting Conditions Outside of the Breathing Circuit.

The closed-circuit heliox delivery system can contain sensors for measuring parameters outside the system, including parameters related to ambient condition or to the physiological state of the user. The sensors can be positioned within the system, on the user, or both.

The closed-circuit heliox delivery system can contain sensors for measuring parameters related to the physiological state of the user. Exemplary sensors include heart rate monitors, grip pressure sensors, cameras, blood pressure monitors, moisture sensors, breathing sensors, brain sensors, etc. The sensors can be a fingertip sensor or wristband worn by the user that measures pulse rate or $CO_2$ levels in the blood. The sensors can be sound sensors or chest bands measuring respiration rate.

The closed-circuit heliox delivery system can also contain sensors for measuring parameters related to the ambient conditions. Sensors can include temperature sensors, humidity sensors, power sensors, etc. For example, a humidity sensor may detect the relative humidity of the ambient air. A power sensor can detect the presence or absence of an external power supply, allowing the controller to respond to a loss of power.

C. Heliox Delivery System Controller

The closed-circuit heliox delivery system contains a controller having an operator interface and a suitable device for processing information or more sensors. The operator interface allows a user to interact or otherwise control the controller and heliox delivery system. The operator interface can have a keypad, buttons, toggles, and/or switches. The operator interface can have an electronic visual display. The visual display can be a light emitting diode (LED) display, organic LED (OLED) display, an active matrix OLED display, a graphical LCD (GLCD), a thin film transistor LCD (TFTLCD), a super TFT LCD, a 7-segment LCD, an in-plane switching LCD (IPSLCD), LED backlit IPS TFT LCD display, a holographic display, a 3-dimensional display, a plasma display, or a combination thereof. The visual display can be touch-screen. The operator interface can be electronically coupled to the controller. Alternatively the operator interface can communicate wirelessly with the controller through a wireless signal such as radio frequency (RF), BLUETOOTH® protocol, optical signal, or other suitable wireless signal. The operator interface can also include a port for connecting to a data storage device such as, but not limited to, a portable computer diskette, a random access memory, a read-only memory, an erasable programmable read-only memory (EPROM or Flash memory), a secured digital (SD) card, and/or, a portable compact disc read-only memory.

The controller contains a processing device suitable for processing information received from the sensors including, but not limited to, a microprocessor that may contain a program that may be implemented in hardware, software, firmware, or a combination thereof. The program may be implemented in microprocessor hardware using any of or a combination of the following technologies, which are well known in the art, including, but not limited to: a discrete logic circuit(s) having logic gates for implementing logic functions upon data signals, an application specific integrated circuit (ASIC) having appropriate combinational logic gates, a programmable gate array(s) (PGA), or a field programmable gate array (FGPA). The processing device can also include a port for connecting to a data storage device such as, but not limited to, a portable computer diskette, a random access memory, a read-only memory, an erasable programmable read-only memory (EPROM or Flash memory), a secured digital (SD) card, or a portable compact disc read-only memory.

The processing device can receive input from a sensor through a direct electrical connection, such as a wire, universal serial bus (USB), or cable. The processing device can receive input from a sensor through an optical connection, such as optical fiber. The processing device can receive input from a sensor through a wireless connection, such as by radio frequency (RF), BLUETOOTH® protocol, or other suitable wireless signal.

The processing device contains a transmitter for transmitting a signal to other components of the heliox delivery system, such as a regulator or a valve. The signal can be electrical, optical, or wireless. The processing device can be connected to other components of the heliox delivery system by a physical connection, such as a wire or cable; an optical connection, such as an optical fiber; or a wireless connection, such as by radio frequency (RF), BLUETOOTH® protocol, or other suitable wireless signal.

The controller can contain one or more alarms. Alarms can be audible, visual, or electronically transmitted alarms or warnings, for example for alerting the user or for alerting a health-care provider. Alarms can include alarms for low pressure, high pressure, fire, power outage, power surge, diminishing gas supplies, system malfunction, system service, etc.

The controller can contain one or more timers, for instance for tracking the time the system has been operating, for tracking a pre-determined shutoff time, for tracking the time since last service, for tracking the time since the gas supplies were changed, etc. The timers can be visually displayed, or in some cases are used to trigger one of the alarms described above or to shut off the system.

FIG. 1 depicts an exemplary closed-circuit heliox delivery system 100, having a breathing bag 101 and two gas supplies (102a, 102b, collectively 102). The breathing bag allows for the patient to take in a deep breath without dropping the pressure in the closed circuit to less than 0 cm $H_2O$. The flow of each of the gases into the breathing bag 101 is individually controlled by a regulator (103a, 103b, collectively 103). A controller 104 is operably connected to a first sensor 105 in the breathing circuit and a second sensor 106 on the user 107. For example, the first sensor 105 may monitor parameters related to pressure, temperature, humidity, etc. while the second sensor 106 monitors heart rate, breathing rate, or blood oxygen levels. The controller 104 adjusts the regulators 103 to adjust gas flow based upon data from the sensors 105,106 to maintain parameters within a targ breathing circuit 108 has a breathing device 109, e.g. a mask, for covering the mouth and nasal passages of the user. The expired gases flow into a $CO_2$ removal system 110 and are returned to the breathing bag 101 to be combined with gases entering from the gas supplies. A humidifier/dehumidifier 111 maintains the gas mixture at a target moisture level.

Figure 2:
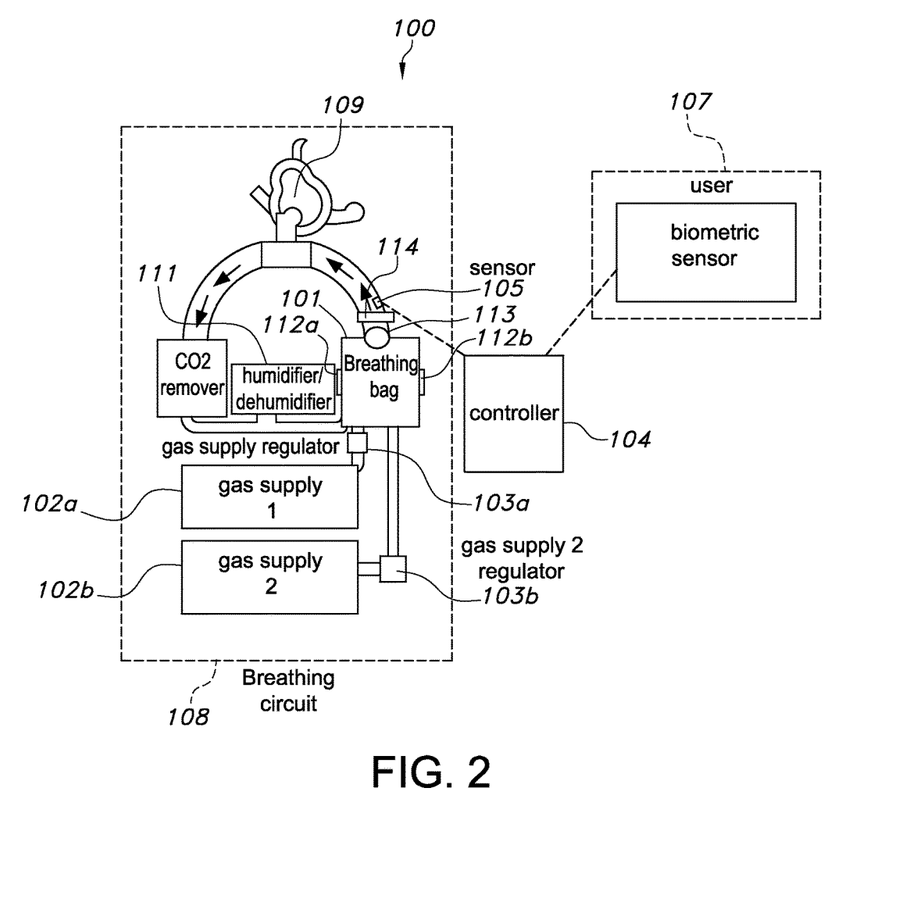
FIG. 2 is a diagram of another exemplary closed-circuit heliox delivery system, similar to FIG. 1, which includes an automated pressure-oxygen servo mechanism (APOSM) to prevent over-pressurization of the system, while ensuring that suitable amount of the gas is delivered to the patient.

FIG. 2 depicts a modification of the system depicted in FIG. 1, and includes one or more sensors for detecting pressure changes in the system and automatically adjusting the regulator(s) to increase the amount of gas supplied to the patient, when needed. Although the system is a 'closed circuit', some gas loss is expected during use, particularly due to removal and replacement of a breathing device 109 (e.g. a mask).

Additionally, the system is preferably designed to allow for controlled release of gas from the circuit to prevent over-pressurization. Preferably the system includes a valve 113 in the breathing bag, which is controlled by the controller, to allow for release of gas from the circuit to prevent over-pressurization. This system ensures that the patient receives a sufficient amount of oxygen, even if a leak is present in the system or if there is no leak in the system and the fractional inspired oxygen concentration (FiO2) levels are in need of replenishment.

If a leak is detected by the sensors, then the controller adjusts the regulators to increase the flow from the one or more gas supplies. Typically the regulator for the oxygen gas supply is increased to replenish the oxygen to target level of FiO2. However, optionally the regulator for the heliox gas supply is adjusted by the controller to increase the rate of heliox flow, alone or in combination with an adjustment to the rate of oxygen flow.

This mechanism may be an automated pressure-oxygen servo mechanism (APOSM). The APOSM system prevents over-distension of the breathing bag, accommodates oxygen entrainment from the gas supply 102, and/or prevents over-pressurization of the circuitry valve function. Excessive pressure in the circuitry could be uncomfortable to the patient and/or pose a safety hazard if the regulator (APSM) were to not function according to design. The mechanical "pop-off" valve can be effected by a spring-loaded system that vents when the pressure exceeds a predetermined value that is customizable to the individual but does cm $H_2O$.

The APOSM senses the state or degree of inflation of the breathing bag 101 via one or more pressure sensors 112a, 112b adjacent to the bag 101, and provides feedback to a servo-controlled regulator 103a and/or 103b that releases gas from the one or more gas supplies 102a, 102b. Preferably the system includes a servo-controlled exhalation port 113, e.g. a valve, on the breathing bag 101 to allow sufficient venting of the system. Optionally, the inlet circuit includes a second safety valve, i.e. a pop-off valve, which automatically releases in the event that the pressure in the closed circuit system exceeds a predetermined safety level. Typically, the pop-off valve will be set to release gas if the system reaches a pressure greater than 30 cm $H_2O$; preferably at pressures lower than 30 cm $H_2O$, such as if the system reaches a pressure greater than 10 cm $H_2O$.

The pop-off safety valve may be located anywhere in the inlet circuit, optionally it is located on breathing bag. In place of two valves, both functions could be performed by a single valve, which (1) responds to the sensors and releases pressure in a controlled manner (and then closes when the pressure decreases below the threshold level) and (2) pops-off automatically, in the absence of a signal from the controller, if system exceeds a predetermined safety level.

The APOSM also receives input from one or more sensors in the inspiratory portion of the circuit. The sensors may measure the partial pressure of oxygen in the inspiratory portion of the circuit. The sensors may also measure the pressure of the breathing bag.

Depending on the data from the pressure sensors, the APOSM sends effector signals to either (a) a regulator to open the gas supply or (b) the exhalation port 113 to open the valve to vent gas to prevent over-distension of the breathing bag 101.

Figure 4:
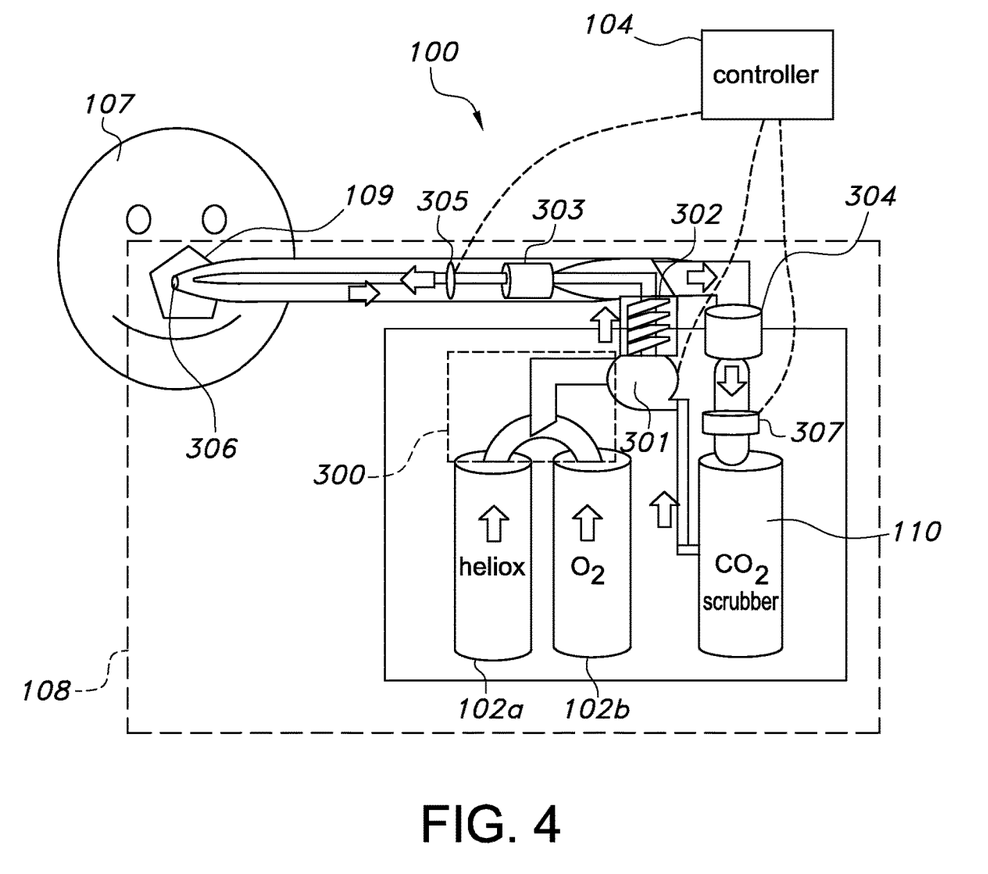
FIG. 4 is a diagram of another exemplary closed-circuit heliox delivery system. Two gas supplies are flowably connected to a regulator where the gases are mixed with air that has passed through a carbon dioxide removal s central regulator controls the mixing of the gases from the gas supplies with air flowing from the carbon dioxide removal device. Air from the gas supplies is mixed prior to being mixed with air flowing from the carbon dioxide removal system. As the user inhales, the mixed gases pass through an air cooler and a humidifier. Expired air passes through a de-humidifier and into the carbon dioxide removal system.

FIG. 4 shows another configuration of the closed circuit heliox delivery system 100. In this configuration, two gas supplies 102a, 102b (collectively 102) (i.e. heliox and oxygen) are flowably coupled to one another and a central regulator 301. The central regulator 301 is operatively coupled to an air cooling device 302. The air cooling device 302 is operatively coupled to a humidifier 303 and in-line humidity and/or temperature sensor 305. The humidifier 303 is operatively coupled to an upper-airway delivery device 109. The upper-airway delivery devi operatively coupled to a dehumidifier 304 and an in-line carbon dioxide sensor 307. The dehumidifier 304 is operatively coupled to a carbon dioxide removal system 110, which is operatively coupled to the central regulator 301. The air cooling device 302 can contain a suitable air coolant. The upper-airway device 109 can have an electromagnetically controlled safety vent 306, such as an air-vent trap or other type of safety valve or vent, to allow the user to inhale air from the external environment.

This safety vent or valve is able to automatically open when there is electrical outage and/or system failure to prevent rebreathing or suffocation.

II. Operation of the Closed-Circuit Heliox Delivery System a. Operation of the Closed Breathing Circuit

In operation, a user breathes through a breathing device 109 that is suitable for use with a closed-circuit breathing system, such as a mask, mouthpiece, or a tracheostomy tube. As the user exhales, air is forced through a first non-return valve, carbon dioxide removal system 110 and into a breathing bag 101, which acts as a counterlung to maintain air pressure within the breathing circuit 108. The carbon dioxide removal system 110 removes carbon dioxide from the exhaled air. As the user inhales, air is drawn from the breathing bag 101 and through a second non-return valve. As the air is drawn into the breathing bag 101, it is mixed with the heliox and oxygen gases. After the air is drawn through the second non-return valve, the heliox and oxygen supplies in the breathing bag 101 are replenished from connected gas supplies 102a, 102b. This cycle is repeated as the user breaths. To account for fluctuating air pressures as a result of the user breathing, the system 100 can contain an in-line "low-pressure" turbine, such as one that generates a pressure of approximately 2 to 4 cm $H_2O$, to keep forward pressure flow.

In some embodiments the system includes an in-line gas cooler 114. See, e.g. FIG. 2. In one embodiment, as the user inhales, air is drawn from the breathing bag 101 and into the gas cooler prior to passing through a second non-return valve. The gases may be mixed in the breathing bag 101 and cooled after exiting the breathing bag, such as depicted in FIG. 2.

Alternatively, the heliox and oxygen gases are mixed in the air cooler as opposed to the breathing bag 101. In this embodiment, the gas cooler is located in the circuit prior to the breathing bag (not shown in Figures). After the through the second non-return valve, the heliox and oxygen supplies in the gas cooler are replenished from connected gas supplies 102. The breathing bag allows for the patient to take in a deep breath without dropping the pressure in the closed circuit to less than 0 cm $H_2O$. The air cooler prevents excessive warm temperature in the breathing circuit.

In some embodiments, there is a combination humidifier/dehumidifier 111 placed at a point along the breathing circuit 108. Preferably, the humidifier/dehumidifier 111 is placed at the ingress or egress of the carbon dioxide removal system, thus controlling humidity of the breathing circuit 108 at the ingress or egress of the carbon dioxide removal system 110. As the user inhales and exhales and as gases are is moved through the breathing circuit 110, the humidifier/dehumidifier 111 adjusts the moisture of the gases accordingly.

As the gases move through the system 100, sensors 105, 106 are continually sensing various conditions of the system 100 or user 107 as described below. These sensors 105,106 send input(s) to the controller 104, which then determines if the conditions in the breathing circuit 108 are within predetermined ranges. If the input indicates that a condition is outside of the predetermined range, the controller 104 sends a signal to the relevant component of the heliox delivery system 100 to bring that condition back to a level or an amount that is within a predetermined range.

In other embodiments (See, e.g. FIG. 4), prior to the reaching the central regulator 301, the gases from the gas supplies 102 are mixed 300. The central regulator 301 functions to combine the mixed gases 300 from the gas supplies 102 with gases flowing from the carbon dioxide removal system 110. As the user inhales, the gases, which include mixed gases 300 from the gas supplies 102 and gases flowing from the carbon dioxide removal system 110, move through an air cooling device 302, through a humidifier 303, past an in-line humidity and/or temperature sensor 305 and into an upper-airway delivery device 109.

Expired air moves through a dehumidifier 304, past an in-line carbon dioxide sensor 307 and into a carbon dioxide removal system 110. The process is repeated when air flows from the carbon dioxide removal system 110 to the central regulator 301, where it is mixed with gases from the gas supplies 102.

As the air moves through the system 100, sensors (e.g. 305, continually sensing various conditions of the system 100 or user 107 as described below. These sensors (e.g. 305, 307) send input(s) to the controller 104, which then determines if the conditions (e.g. humidity or carbon dioxide level) in the breathing circuit 108 are within predetermined ranges. If the input indicates that a condition is outside of the predetermined range, the controller 104 sends a signal to the relevant component (e.g. the central regulator 301) of the heliox delivery system 100 to bring that condition back to a level or an amount that is within a predetermined range.

b. Control of Closed Circuit Heliox Delivery System

In operation, the controller 104 receives input from a sensor 105, 106 and determines if the input received lies within a predetermined range of values. The predetermined range represents the tolerated range of values for any given condition. If the input received lies outside of the predetermined range of values, then the controller 104 sends a signal to elicit a response in a component of the breathing circuit 108 to bring the input within the range of predetermined values. The controller 104 continually receives input from the sensors 105, 106, evaluates the input, and sends signals to control the components of the heliox delivery system 100.

As an example, if the controller 104 receives a partial pressure of oxygen that is lower than the lowest value in the predetermined range, then in response, the controller 104 signals the regulator 103 on an oxygen supply, to allow for increased oxygen influx into the breathing circuit 108 to bring the partial pressure of oxygen within the predetermined range. Once the partial pressure of oxygen is within the predetermined range, the controller 104 ceases to signal the regulator 103, thereby reducing oxygen influx into the breathing circuit 108.

i. Predetermined Ranges

The predetermined ranges for each condition measured by a sensor 105, 106 can vary depending on the disease or symptoms suffered by the user as well as physiological characteristics of the user 107. The predetermined range can be set to define any range of values. Preferably, the predetermined range is defined by an upper limit value and a lower limit value. Threshold values may be created by creating a range extending from a single integer to either positive or negative infinity. Typically in the treatment of airway disorders, the predetermined ranges are determined by a prescribing physician or other medical personnel.

The predetermined ranges can be manually set by the user or can otherwise be preprogrammed into the closed-circuit heliox delivery system 100. For example, a physician, pharmacist, or other medical personnel may preprogram the system 100 according to a prescribed treatment protocol. This may be done directly by the physician, pharmacist, or other medical personnel or the physician, pharmacist, or other medical personnel may communicate with the controller 104 remotely via an Internet connection, telephone connection, or other remote communication method. In some instances, the prescribed treatment protocol containing the predetermined ranges may be on a portable data storage device, such as a flash drive, which may be then given to the user 107 by their physician. The user can then insert the flash drive into a suitable port on the controller 104, thus providing the predetermined ranges to the controller 104. In other instances, the system can be delivered from the manufacturer preprogrammed.

The predetermined ranges can be password protected, thus restricting who may alter the treatment protocol to someone authorized to do so, such as a prescribing physician or agent thereof.

a. Heliox

Heliox treatments have been used to treat various diseases and symptoms that afflict the airway, including, but not limited to COPD, asthma, upper airways obstruction, and croup. See Reuben and Harris, *Emerg Med J,* 21: 131-135 (2004). The predetermined ranges reflect differences in treatment and symptoms experienced by the user 107 and by physiological characteristics of the user 107. Insofar as heliox contains helium and oxygen, and the ratio of the two components is often important to achieving a desired effect, preferably predetermined ranges are set for both helium and oxygen, or any other supplied gas.

i. Helium

The upper limit value and lower limit value for the predetermined range for helium can be any suitable value. Preferably, the upper limit value and lower limit values of the predetermined range are set to keep helium concentration within the breathing circuit 108 at any concentration or concentrations between 50 and 79%. Insofar as there are primarily only two sources of gases being mixed and delivered to the user (i.e., heliox and oxygen), the concentration, partial pressure helium within in the circuit can be indirectly determined based on the concentration, partial pressure, or volume of oxygen, which is constantly directly measured. Indirect determination of helium amount is a feasible and cost-effective way to measure helium concentrations within the system 100. Alternatively, the amount of helium could be directly measured using a sensor.

The predetermined ranges may be adjusted accordingly based on the type of input received. Alternatively, the controller 104 may be configured to convert the units of input into another unit type to be used with a predetermined range. For example, if the input is the partial pressure of oxygen, and the predetermined helium range is based on the concentration of oxygen, the controller 104 may be configured to convert the partial pressure of oxygen input into a concentration of oxygen value to be used to indirectly determine if the amount of helium within the breathing circuit 108 is correct.

ii. Oxygen

The upper limit value and lower limit value for the predetermined range for oxygen can be any suitable value. Preferably, the upper limit value and lower limit values of the predetermined range are set to keep oxygen concentration within the breathing circuit 108 at any concentration or concentrations between 21 and 50%. As one having ordinary skill will appreciate, any measure of the amount of oxygen may be used, such as, but not limited to concentration, partial pressure, or volume. The predetermined ranges may be then adjusted accordingly based on the type of input received. Alternatively, the controller 104 may be configured to convert the units of input into another unit type to be used with a predetermined range. For example, if the input is the partial pressure of oxygen and the predetermined range is based on the concentration of oxygen, the controller 104 may be configured to convert the partial pressure input into a concentration value to be used to determine if the amount of oxygen in the breathing circuit 108 is correct.

b. Carbon Dioxide

The only source of carbon dioxide is that generated by the user 107. The amount of carbon dioxide (e.g. concentration or partial pressure) within the breathing circuit is continuously measured. This measurement serves primarily two purposes: (1) as a safety monitor to prevent dangerous build of carbon dioxide breathing circuit and (2) to monitor the level of functionality of the carbon dioxide removal system. The upper limit value and lower limit value for the predetermined range for carbon dioxide can be any value from negative infinity to positive infinity. Preferably, the upper limit value and lower limit values of the predetermined range are set to keep partial pressure of carbon dioxide within the breathing circuit 108 at any partial pressure not to exceed 30,000 parts per million (ppm) for more than fifteen minutes and not to exceed 10,000 ppm over an 8-hour period. As one having ordinary skill will appreciate, any measure of the amount of carbon dioxide may be used, such as, but not limited to concentration, partial pressure or volume. The predetermined ranges may be then adjusted accordingly based on the type of input received. Alternatively, the controller 104 may be configured to convert the units of input into another unit type to be used with a predetermined range. For example, if the input is the partial pressure of oxygen and the predetermined range is based on the concentration of oxygen, the controller 104 may be configured to convert the partial pressure input into a concentration value to be used to determine if the amount of oxygen in the breathing circuit 108 is correct.

c. Humidity

Humidity is important to regulate because inhaled air that is to arid can cause drying of the mucous membranes in the airway and lead to discomfort and infection due to the deterioration of the membrane barrier. In contrast, too great a humidity can lead to the development of mold within the components of the breathing circuit, which then can be inhaled by the user and cause disease. The upper limit value and lower limit value for the predetermined range for oxygen can be any suitable value. Preferably, the upper limit and the lower limit values of the predetermined range for humidity are set to maintain a relative humidity of any percent between 25 and 80%.

d. Air Pressure

The system 100 relies upon a delivering heliox under low pressure within a positive-airway pressure system. Thus, preferably the total air pressure within the breathing system is less than 4 cm $H_2O$ (approximately 0.392 kPa). Preferably, the upper limit and lower limit of the predetermined range is set such that the air pressure within the breathing circuit 108 is less than 4 cm $H_2O$ but greater than approximately 2 cm $H_2O$.

ii. Control of the Heliox Delivery System in Response to Processing of Sensor Input.

After sensor input is received by the controller 104, the controller 104 converts units as required and then compares the input to the appropriate predetermined range. If the input is determined by the controller 104 to be outside of the predetermined range, then the controller 104 sends a signal to the appropriate component of the heliox delivery system 100 to bring the input within the predetermined range. The signal sent by the controller 104 can be any form of signal, including but not limited to mechanical, electrical, or wireless including radio frequency, digital, Wi-Fi, or optical signals.

a. Control of Gas Influx

If the amount of helium is determined to be outside the predetermined range set for helium, the controller 104 sends a signal to the regulator 103 controlling the flow of heliox from the heliox supply to either increase the influx of helium or decrease the influx of helium such that the amount of helium is brought back to within acceptable limits. If the amount of oxygen is outside the predetermined range, the controller 104 sends a signal to the regulator 103 controlling the flow of oxygen to either increase or reduce the flow of oxygen accordingly to bring the amount of oxygen to within the predetermined range. If heliox is provided in a single tank, then if the amount of heliox is outside the predetermined heliox range, the controller 104 can send a signal to the regulator 103 controlling the influx of heliox into the breathing circuit 108 to increase or reduce the flow of heliox into the system.

b. Control of Gas Removal

In the event that the amount of carbon dioxide is outside the upper limit of the predetermined carbon dioxide range, the controller 104 can send signal causing a carbon dioxide removal system to be engaged and remove excess carbon dioxide from the breathing circuit 108. Alternatively, the controller 104 can signal a valve on the 108 breathing circuit to open to release carbon dioxide into the external atmosphere. When the amount of carbon dioxide has returned to be within the predetermined range, the controller 104 can signal the valve to close.

If the amount of oxygen within the breathing circuit 108 exceeds the upper limit of the predetermined range, then the controller 104 can signal breathing circuit to open to release the gas mixture into the external atmosphere, signal the regulator 103 to decrease the influx of oxygen into the breathing circuit 108, or both. When the amount of oxygen has returned to being within the predetermined range, the controller 104 can signal the valve to and/or the regulator 103 to return to their previous state or level of functioning. Because oxygen is consumed by the user 107 and the opening of a valve in the breathing circuit also results in helium, which is expensive, being exhausted into the external atmosphere, it is preferable that oxygen levels be controlled by controlling the influx of oxygen.

Excess carbon dioxide must be avoided because of unwanted and life threatening effects of high levels of carbon dioxide exceeding 30,000 ppm in any consecutive 15-minute time period or 10,000 ppm over an 8-hour time period. When properly functioning, the amount of carbon dioxide is maintained below approximately 10,000 ppm by the carbon dioxide removal system 110. However, in the event the carbon dioxide removal system 110 is insufficient to keep the amount of carbon dioxide below the 10,000 kPa threshold, then the controller 104 can signal a valve to be opened, allowing excess carbon dioxide to be released into the external atmosphere.

c. Control of Humidity

Preferably, the closed-circuit heliox delivery system contains a combination humidifier/dehumidifier 111. Preferably, if the relative humidity, is outside of the predetermined range, then the controller 104 sends a signal to the combination humidifier/dehumidifier 111 to adjust action of the combination humidifier/dehumidifier 111 accordingly. Alternatively, in embodiments employing only a humidifier, when the relative humidity in the breathing circuit 108 is greater than the upper limit of the predetermined range, the controller 104 signals a valve to open, exposing the breathing circuit 108 to the external atmosphere and ideally reducing humidity within the breathing circuit 108. When the relative humidity is brought within the predetermined range, the controller 104 sends a signal to the valve to close the valve. In these embodiments, if the relative humidity is less than the lower limit of the predetermined range, then the controller 104 sends a signal to the humidifier causing the humidifier to increase the relative humidity within the breathing circuit. When the relative humidity has been corrected, t signals the humidifier to reduce or cease operation.

d. Control of a Safety Valve

In the event that the controller 104 is not operating properly, the breathing circuit 108 contains a valve, such as a low pressure or low flow release valve, which does not require any controller 104 action. In some embodiments, the valve may be configured to respond directly to a build-up of a gas above a threshold or respond to an overall increase or decrease in air pressure within the breathing circuit 108. Upon the triggering event, (e.g. too much pressure or carbon dioxide) the valve opens resulting in opening the breathing circuit 108 to the external atmosphere. This feature is important particularly if/when the system is used with unconscious individuals, who are unable to remove the mask in the event of system malfunction.

The valve may be a pop-off valve, optionally attached to the breathing bag.

e. Control of the System in Response to Biometric or Environmental Input

In some embodiments, biometric sensors 106 are employed to detect physiological states in the user 107. The controller 104 can be-configured to send signals to adjust the relevant component of the circuit in response to input from the biometric sensors 106. For example, a pulse oximeter may be used to sense a user's blood oxygen concentration. If the input received by the controller 104 from the pulse oximeter is lower than the lower limit value of the predetermined range, then the controller 104 can send a signal to the oxygen regulator to increase the influx of oxygen into the breathing circuit 108.

In one embodiment, the system can be used to modify the core temperature of a patient's body, such as by delivering cooled gases to the patient. Modifying a patient's core body temperature can facilitate sleep or ameliorate the body's inflammatory response. The patient's temperature could be determined using one or more sensors. For example biometric sensors on the patient can be used to communicate temperature information to the controller. Additionally or alternatively, the system may include a temperature sensor in the expiratory circuit, which measures the temperature of the exhaled gases as they exit the upper-airway delivery device 109. The temperature of the inhaled gases can be modified in any desired manner. For example, the temperature can change in a circadian manner to ameliorate inflammation in the patient.

The system may include a spirometer for measuring the patient's airflow. The spirometer may be an in-line device that is integrated with the breathing circuit. Exemplary spirometers include pneumotachographs, turbine spirometers, and ultrasound spirometers. Suitable spirometers are known to those of ordinary skill in the art.

In some embodiments, environmental sensors sense environmental conditions outside the breathing circuit 108, such as environmental humidity and temperature, which may affect the system 100. In response to input from these environmental sensors, the controller 104 can be configured to adjust the relative condition within the breathing circuit 108 accordingly.

f. Alerts

In some embodiments, the controller 104 also provides alerts or alarms when an amount of a gas, humidity, air pressure, or other parameter is outside the relevant predetermined range. The alarm or alert can be any audible or visible signal, or communication, electronic or otherwise. The alert or alarm can be configured to alert the user or someone within the range of sight or sound, thus allowing the individual to take action if necessary. In some embodiments, the controller 104 can alert a remote individual, such as via text message, email, or automated phone call.

Figure 3:
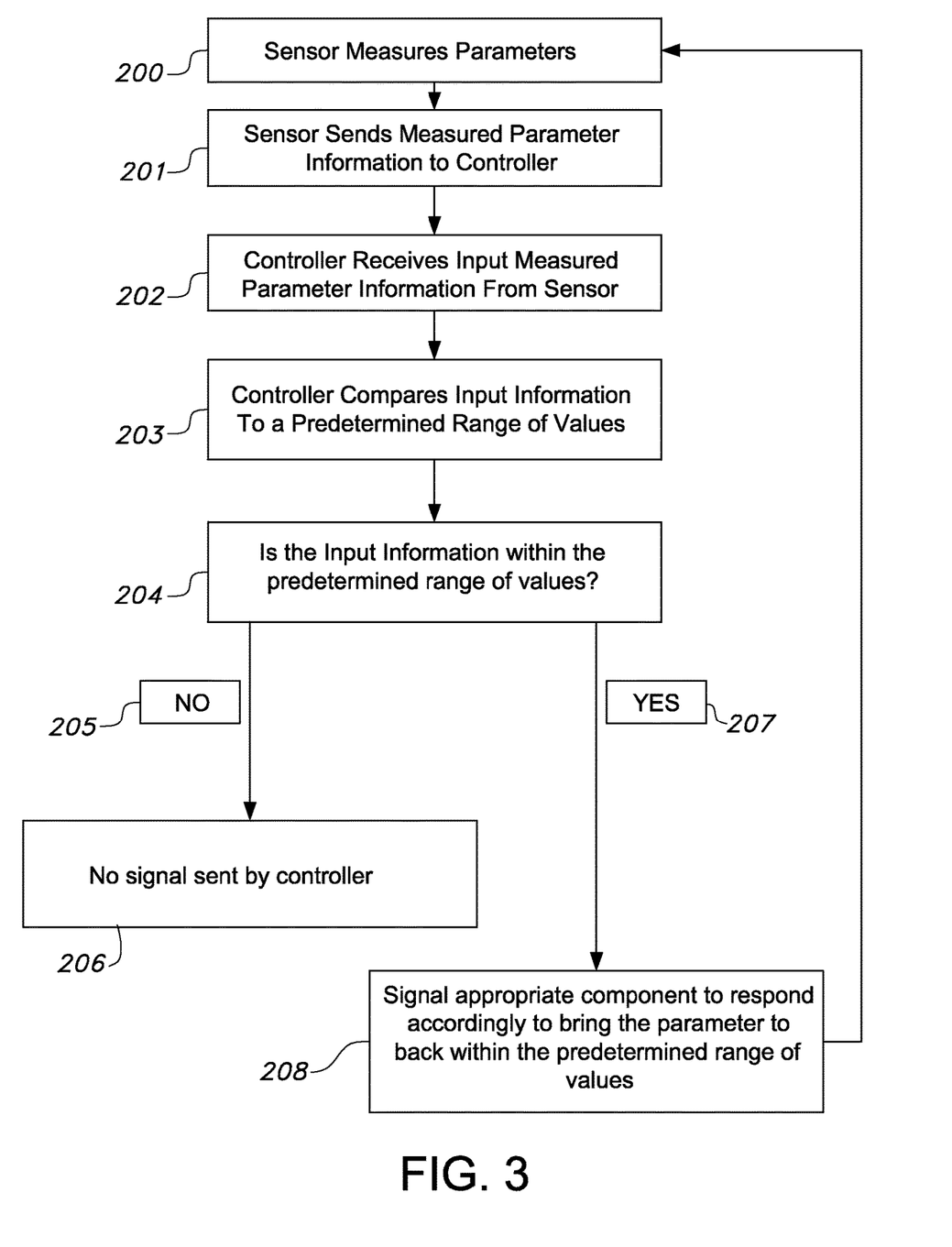
FIG. 3 is a logic diagram for controlling a closed-circuit heliox delivery system. The sensor(s) measure one or more parameters, sending information about the measured parameters to the controller. The controller receives one or more parameters from the sensors and compares these to a predetermined range of values.

FIG. 3 depicts a flow chart of one embodiment for the control of a closed-circuit heliox delivery system 100. The sensor 105,106, measuring one or more parameters 200, sends 201 the measured values to the controller 104. The controller 104, receiving the information from the sensors 202, compares 203 the values to a predetermined range of values to determine 204 if the input information lies within the predetermined range of values. If the measured values fall within the predetermined range 205, no signal is sent by the controller 206. If the measured values fall outside 207 the predetermined range, the controller signals the appropriate components of the system to adjust the parameters and bring the values back within the predetermined range 208. The process can be repeated as necessary. Optionally, the system includes a safety valve to release pressure in the closed-circuit in case the controller or regulator fails. For example, the safety valve could be a pop off valve that automatically releases if a pressure exceeds a certain threshold optionally in the breathing bag.

III. Use of the Closed Circuit Heliox Delivery System

The closed circuit heliox delivery system can be used to treat or relieve airway diseases, disorders, and symptoms, particularly upper-airway diseases, disorders, and symptoms. Exemplary conditions to be treated include, but are not limited to chronic obstructive pulmonary disease (COPD), asthma, bronchiolitis, and croup. Heliox treatment parameters can vary based on disorder, disease or symptom treated, as well as user physiologic characteristics.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An in-home, closed-circuit heliox delivery system that allows a user to breathe normally, comprising:
   (i) one or more gas supplies, wherein the one or more gas supplies comprise a heliox supply source or a helium and oxygen supply sources;
   (ii) one or more regulators, wherein one of the one or more regulators is operatively coupled to one of the one or more gas supplies;
   (iii) an upper airway device;
   (iv) a breathing circuit comprising
      a breathing bag, wherein the breathing bag is configured to prevent a pressure in the breathing circuit from decreasing to less than 0 cm $H_2O$, wherein the breathing bag is in fluid communication with the one or more gas supplies,
      an inspiratory conduit, wherein the inspiratory conduit is in fluid communication with the breathing bag and the one or more gas supplies,
      an expiratory conduit, wherein the expiratory conduit is configured to receive expired gases from the upper airway device, and
      a carbon dioxide removal system, wherein the carbon dioxide removal system is configured to receive the expired gases exiting the expiratory conduit and is in fluid communication with the breathing bag and/or the inspiratory conduit,
      wherein the inspiratory conduit and the expiratory conduit are in fluid communication with the upper airway device,
   wherein the one or more regulators are configured to control a rate of gas flowing out of the one or more gas supplies and direct gas from the one or more gas supplies into the breathing bag and/or into the inspiratory conduit;
   (v) a first sensor, the first sensor being operatively coupled to the breathing circuit; and
   (vi) a controller in electrical communication with the breathing circuit, wherein the controller is configured to receive input from the first sensor and control operation of the breathing circuit in response to the received input from the first sensor,
   wherein the controller is programmed such that while the user is breathing, a total air pressure of the breathing circuit is less than 4 cm $H_2O$, and
   wherein while the user inhales, the total air pressure of the breathing circuit does not decrease below 0 cm $H_2O$.

2. The closed-circuit heliox delivery system of claim 1, further comprising a valve that opens upon receiving a stimulus, wherein the opening of the valve exposes the breathing circuit to the external atmosphere.

3. The closed-circuit heliox delivery system of claim 1, wherein the first sensor senses an amount of oxygen within the breathing circuit.

4. The closed-circuit heliox delivery system of claim 1, wherein the first sensor senses an amount of carbon dioxide within the breathing circuit.

5. The closed-circuit heliox delivery system of claim 1, wherein the first sensor senses air pressure within the breathing circuit.

6. The closed-circuit heliox delivery system of claim 1, wherein the first sensor senses humidity within the breathing circuit.

7. The closed-circuit heliox delivery system of claim 1, further comprising a humidifier and/or dehumidifier, the humidifier and/or dehumidifier being operatively coupled to the breathing circuit.

8. The closed-circuit heliox delivery system of claim 1, further comprising a release valve, the release valve being operatively coupled to the breathing circuit.

9. The closed-circuit heliox delivery system of claim 1, wherein the one or more gas supplies comprise a tank.

10. The closed-circuit heliox delivery system of claim 9, wherein the one or more regulators is operatively coupled to the tank.

11. The closed-circuit heliox delivery system of claim 1, further comprising a second sensor, the second sensor being operatively coupled to the controller and independent from the breathing circuit.

12. The closed-circuit heliox delivery system of claim 11, wherein the second sensor senses a physiologic state of a user.

13. The closed-circuit heliox delivery system of claim 11, wherein the second sensor senses a condition of the environment outside of the breathing circuit.

14. The closed-circuit heliox delivery system of claim 1, further comprising one or more pressure sensors adjacent to the breathing bag, wherein the one or more pressure sensors are operatively coupled to the controller.

15. The closed-circuit heliox delivery system of claim 14, wherein the system further comprises a valve, configured to open and close in response to the one or more pressure sensors to prevent over-pressurization of the system.

16. The closed-circuit heliox delivery system of claim 1, wherein the upper airway device comprises an electromagnetically controlled safety valve, wherein the electromagnetically controlled safety valve opens when an electrical outage and/or system failure occurs.

17. The closed-circuit heliox delivery system of claim 1, wherein the controller is programmed such that while the user is breathing, the total air pressure of the breathing circuit is between 2 cm $H_2O$ and 4 cm $H_2O$.

18. A method for delivering heliox to a patient in need thereof under low pressure using an in-home, closed-circuit heliox delivery system,
wherein the heliox delivery system is the system of claim 1,
wherein the method comprises
(i) flowing the gas from the one or more gas supplies into the breathing circuit as the patient breathes normally through the upper airway device, wherein the total air pressure of the breathing circuit is between 0 and 4 cm $H_2O$.

19. The method of claim 18 further comprising:
(ii) receiving the input from the first sensor;
(iii) determining whether the received input from the first sensor is within a predetermined range; and
(iv) controlling the closed-circuit heliox delivery system in response to determining whether the received input is within a predetermined range.

20. The method of claim 19, wherein the received input is a partial pressure of helium, oxygen, or carbon dioxide within the breathing circuit.

21. The method of claim 19, wherein the received input is a relative humidity within the breathing circuit.

22. The method of claim 19, wherein step (iv) comprises the controller opening and closing a valve to prevent over-pressurization of the system.

23. The method of claim 19, wherein step (iv) comprises the controller adjusting the one or more regulators to adjust gas flow from the one or more gas supplies to the patient.

24. The method of claim 18, wherein the system further comprises a second sensor and wherein the second sensor is independent of the breathing circuit of the closed-circuit heliox delivery system.

25. The method of claim 24, wherein the second sensor measures a physiologic state of a user.

26. The method of claim 24, wherein the second sensor measures a condition of the environment outside of the breathing circuit.

27. The method of claim 18, further comprising delivering to the patient an amount of one or more therapeutic agents.

28. The method of claim 27, wherein the delivering step occurs in response to data characterizing a physiologic state of the patient.

29. The closed-circuit heliox delivery system of claim 1, wherein the upper airway device is a mask that covers a mouth and nasal openings of the user.

30. The closed-circuit heliox delivery system of claim 1, wherein the breathing circuit further comprises a gas cooler, wherein the gas cooler is in fluid communication with the inspiratory conduit.

* * * * *